United States Patent [19]

Fruchey

[11] Patent Number: 4,999,457

[45] Date of Patent: Mar. 12, 1991

[54] PROCESS FOR THE SYNTHESIS OF 3-CHLORO-4-HYDROXYACETANILIDE

[75] Inventor: Olan S. Fruchey, Corpus Christi, Tex.

[73] Assignee: Hoechst Celanese Corporation, Somerville, N.J.

[21] Appl. No.: 478,294

[22] Filed: Feb. 8, 1990

Related U.S. Application Data

[63] Continuation-in-part of Ser. No. 153,756, Feb. 8, 1988.

[51] Int. Cl.$^5$ ..................... C07C 233/25; C07B 43/06
[52] U.S. Cl. .................................................. 564/223
[58] Field of Search ............... 564/223, 412; 568/779; 570/209

[56] References Cited

U.S. PATENT DOCUMENTS 2,759,981  8/1956  Pray et al. ........................... 568/779
4,210,765  7/1980  Mark ................................ 568/637 X
4,310,702  1/1982  Masilammi et al. ................ 568/348
4,439,595  3/1984  Chiang ........................... 568/779 X
4,439,596  3/1984  Irwin ............................. 568/779 X

OTHER PUBLICATIONS

Masilammi et al., J. of Org. Chem., 46(22), 4486–4489, Oct. 1981.
Neckers & Doyle, Organic Chemistry, John Wiley & Sons, Inc., 1977, pp. 668–669.

*Primary Examiner*—Carolyn S. Elmore
*Attorney, Agent, or Firm*—DePaoli & O'Brien

[57] ABSTRACT

A novel process for the preparation of 3-chloro-4-hydroxyacetanilide in high yields is disclosed which involves reacting N-acetyl-para-aminophenol (APAP) with sulfuryl chloride ($SO_2Cl_2$) as the chlorine source and liquid $SO_2$ as the reaction medium.

5 Claims, No Drawings

PROCESS FOR THE SYNTHESIS OF 3-CHLORO-4-HYDROXYACETANILIDE

CROSS-REFERENCE TO RELATED APPLICATIONS

This application in a Continuation-in-part of Ser. No. 153,756, filed Feb. 8, 1988.

BACKGROUND OF THE INVENTION

This invention is concerned with the novel process for the production of 3-chloro-4-hydroxyacetanilide (CAPAP) in high yields by the chlorination of N-acetyl-para-aminophenol (APAP) using sulfuryl chloride ($SO_2Cl_2$) as the chlorine source and liquid sulfur dioxide as the reaction medium.

The process of this invention provides a very easy and relatively inexpensive synthesis for the production of CAPAP.

DESCRIPTION OF THE PRIOR ART

CAPAP is a known compound which has been very difficult to prepare perhaps due to the fact that the monochlorination of phenolics is difficult to accomplish.

One reported CAPAP synthesis involves treating 3-chloroacetanilide with rabbit liver microsomes. See Daly et al, Biochem. Pharmacol., 17(1), 31–6, 1968 (CA 68 13:56878p)

CAPAP has been observed as a metabolic intermediate from phenacetin which is a known analgesic. See for example Calder et al, the Australian Journal of Chemistry, Vol. 29, No. 8, pp. 1801–8, 1976; (CA 85 21:153705p) as Well as Calder et al, Chem-Biol Interactions, Vol. 8, No. 2, pp. 87–90, 1974 (CA 80 15:82342b). It is reasonable to assume that CAPAP would have analgesic properties. Additionally, CAPAP finds utility in the field of low molecular weight liquid crystal materials and in the formation of liquid crystal polymers.

CAPAP is formed in small amounts during the Beckmann rearrangement of 4-hydroxyacetophenone oxime using thionyl chloride in liquid sulfur dioxide to produce APAP as disclosed and claimed in U. S. Pat No. 4,524,217.

A method to prevent the formation of CAPAP is said Beckmann rearrangement as disclosed and claimed in co-pending application Ser. No. 118,117, filed Nov. 6, 1987, entitled "A Novel Process to Prevent Formation of Chlorinated By-Products in APAP Production," the disclosure of which is incorporated by reference.

DESCRIPTION OF THE PREFERRED EMBODIMENTS

The novel process of this invention is carried out simply by treating APAP with sulfuryl chloride as a slurry in liquid sulfur dioxide as the reaction medium. The reaction is usually carried out at room temperature in order to prevent dichlorination and temperatures ranging from 0°–50° C. are suitable. A preferred temperature ranges from 0°–30° C. Particularly preferred is to operate between 20° and 25° C. The reaction is carried out at autogenous pressure.

APAP is soluble in liquid sulfur dioxide in only small amounts, i.e., about 2 wt.%. It is not known whether the reaction is occurring in the solid phase or in solution with the APAP rapidly coming into and out of solution. Accordingly, no additional reaction medium for APAP is used in the novel process of this invention.

The ratio of APAP to $SO_2Cl_2$ on a molar basis is usually 1:1. It is to be understood that higher molar ratios can be used such as 1:2 or higher but no practical benefits are gained going beyond substantially 1:1 molar ratios. The amount of $SO_2$ which is employed is also not narrowly critical and sufficient $SO_2$ must be used to function as a reaction medium and form a slurry. Conventionally, 5 lbs. of liquid $SO_2$ are used for each pound of APAP.

It is to be immediately understood that the chlorination of APAP by the novel process of this invention to produce CAPAP in high yields is not predictable or even fully understood. As will be illustrated in the comparative examples, when other conventional chlorinating agents are used, a very inferior process results in connection with extremely low yields and other undesirable features.

The following examples will not illustrate the novel process of this invention.

EXAMPLE 1

A 1 liter 316 SS Zipperclave was charged with 150 g of APAP. The autoclave was cooled to −50° C. with a Dry Ice-acetone bath and 500 g sulfur dioxide was vacuum transferred into the autoclave forming a slurry. Eighty ml of sulfuryl chloride was added via a syringe and the contents of the autoclave were allowed to warm to room temperature; the slurry was allowed to stand at room temperature overnight and then the sulfur dioxide was vented. The reactor solids were slurried with 450 ml of hot acetone and then the slurry was cooled in an ice bath, filtered and washed with 2-200 ml portions of cold acetone to obtain offwhite CAPAP.

The off-white solids were placed in a 2-L beaker with 1 g citric acid, 1 g sodium dithionite and 1000 mL demineralized water and heated to dissolve all the solids. The beaker was then placed in an ice bath and crash crystallized to 20° C. with stirring. The solids were filtered and washed with 2-200 mL portions of cold water. The wet solids were dried on the rotabap at 60° C. for 30 minutes yielding 104.8 g of white solids (CAPAP).

Further Purification

The solids were then placed in a 2-L round bottom flask with 750 mL of demineralized water, 0.3 g sodium dithionite, and 1 g ADP carbon (Calgon lot D-06126) and were heated and allowed to reflux for 30 minutes.

The contents of the flask were then hot filtered through a celite pad into 0.1 g sodium dithionite. The filtrate was crash crystallized in an ice bath to 20° C.

The white crystals were filtered and washed with 200 mL of demineralized water. The solids were finally dried on the rotavap at 60° C. for 30 minutes yielding 74.3 g of CAPAP (melting point 133°–135° C.). No polychlorinated material is detected.

Examples 2 and 3 are presented in order to demonstrate that other conventional chlorination procedures are inferior.

EXAMPLE 2

A chlorine generator was assembled by placing 100 mL of concentrated HCl in an addition funnel and attaching the funnel via a vacuum sidearm adapter to a round-bottom flask which contained 32 g of potassium permanganate.

A chlorine generator gas line was connected to a sintered glass gas sparger which was inserted into a three-necked round-bottom flask. APAP (30 g) and water (150 mL) were charged to the three-necked round-bottom flask and the contents were stirred.

HCl was dripped slowly over a 25 minute period into the potassium permanganate in order to generate chlorine. The APAP solution turned black during this time.

The APAP water solution was then dried on a rotavap yielding a black tarry residue which was shown to contain about 12% CAPAP.

EXAMPLE 3

The procedure of Example 2 was repeated with the exception that the chlorination reactor was charged with 80 mL of concentrated HCL and 13 g of potassium permanganate.

The 30 g of APAP were charged to the three-necked round-bottom glass with 100 mL of methanol as opposed to the water which was used in Example 2. The three-necked flask was placed in an ice bath and the contents stirred.

The HCl was dripped into the chlorine generator slowly and the reaction flask allowed to stand stirring for 1 hour after completion. Again, the APAP solution turned black during chlorine addition. The methanol was rotavapped off yielding a black tarry residue which contained about 8% of CAPAP.

Examples 2 and 3 clearly demonstrate that not all conventional chlorination procedures result in the production of CAPAP at high yields and that the chlorination procedure of the novel process of this invention is unobvious.

What is claimed is:

1. A process for the production of 3-chloro-4-hydroxyacetanilide in high yields which comprises reacting a mixture consisting essentially of N-acetyl-para-aminophenol with sulfuryl chloride as a slurry in a reaction medium of liquid sulfur dioxide at a temperature from 0°–50° C. under autogenous pressure.

2. The process of claim 1 wherein the temperature ranges from 0°–25° C.

3. The process of claim 1 wherein the temperature is about 20°–25° C.

4. The process of claim 1 wherein the mol ratio of N-acetyl-para-aminophenol to sulfuryl chloride is about 1:1.

5. The process of claim 4 where about 5 pounds of liquid $SO_2$ is employed per pound of APAP.

* * * * *